United States Patent
Wang et al.

(10) Patent No.: US 11,246,945 B2
(45) Date of Patent: Feb. 15, 2022

(54) CISPLATIN-LOADED MICROBUBBLES, PHARMACEUTICAL COMPOSITION FOR TREATMENT OF CANCER, METHOD FOR PREPARING PHARMACEUTICAL COMPOSITIONS AND METHOD FOR TREATING CANCER

(71) Applicant: National Defense Medical Center, Taipei (TW)

(72) Inventors: Chih-Hung Wang, New Taipei (TW); Ai-Ho Liao, Taipei (TW); Hang-Kang Chen, New Taipei (TW)

( * ) Notice: Subject to any disclaimer, the term of this patent is extended or adjusted under 35 U.S.C. 154(b) by 0 days.

(21) Appl. No.: 16/434,647

(22) Filed: Jun. 7, 2019

(65) Prior Publication Data

US 2020/0384123 A1 Dec. 10, 2020

(51) Int. Cl.
| | |
|---|---|
| *A61K 47/69* | (2017.01) |
| *A61K 33/243* | (2019.01) |
| *A61P 35/00* | (2006.01) |
| *A61K 9/00* | (2006.01) |
| *A61K 9/50* | (2006.01) |
| *A61K 41/00* | (2020.01) |

(52) U.S. Cl.
CPC ........ *A61K 47/6925* (2017.08); *A61K 9/0009* (2013.01); *A61K 9/5052* (2013.01); *A61K 9/5089* (2013.01); *A61K 33/243* (2019.01); *A61K 41/0028* (2013.01); *A61P 35/00* (2018.01)

(58) Field of Classification Search
CPC . A61K 47/6925; A61K 33/243; A61K 9/5052
See application file for complete search history.

(56) References Cited

U.S. PATENT DOCUMENTS

| | | | | |
|---|---|---|---|---|
| 5,932,248 | A | * 8/1999 | Chen ................ | A61K 47/52 424/486 |
| 2001/0031243 | A1 | * 10/2001 | Unger ............... | A61K 49/227 424/9.51 |
| 2011/0044903 | A1 | * 2/2011 | Borrelli ............. | A61K 49/223 424/9.1 |

FOREIGN PATENT DOCUMENTS

| | | |
|---|---|---|
| CN | 1343118 A | 4/2002 |
| CN | 101005858 A | 7/2007 |
| CN | 105560230 A | 5/2016 |
| TW | I616210 B | 3/2018 |
| TW | I620563 B | 4/2018 |
| WO | WO 2002/072011 A2 | 9/2002 |

OTHER PUBLICATIONS

Ferraro et al, "Cisplatin binding to human serum albumin: a structural study", ChemComm, www.rsc.org/chemcomm, pp. 1-4.

Ivanov et al., "Cisplatin Binding Sites on Human Albumin", The Journal of Biological Chemistry, vol. 273, No. 24, Issue of Jun. 12, pp. 14721-14730, 1998.

Gonias et al., Complexes of Serum Albumin and cis-Dichlorodiammineplatinum (II), The Journal of Biological Chemistry, vol. 258, No. 9, Issue of May 10, pp. 5764-5769, 1983.

Pizzo et al., "Selectivity and Stereospecificity of the Reactions of Dichlorodiammineplatinum (II) with Three Purified Plasma Proteins", Journal of Inorganic Biochemistry 33, 67-76 (1988), Elsevier Science Publishing Co., Inc.

Aharon Gedanken, "Preparation and Properties of Proteinaceous Microspheres Made Sonochemically", Chem. Eur., J 2008, 143, 2840-3853.

Lee et al., "Cisplatin loaded albumin mesospheres for lung cancer treatment", Am. J. Cancer Res. 2015, 5(2):603-615.

Chen et al., "The role of poly(ethylene glycol) brush architecture in complement activation on targeted microbubble surfaces", Biomaterials 32, 2011, 6579-6587.

Chen et al., "Effect of surface architecture on in vivo ultrasound contrast persistence of targeted size-selected microbubbles", National Institute of Health, Ultrasound Med Biol. Mar. 2012, 38(3), 492-503.

Garg et al., "The effect of lipid monolayer in-plane rigidity on in vivo microbubble circulation persistence", Elsevier, Biomaterials 34, 2013, 6862-6870.

Alexander L. Klibanov, "Ligand-Carrying Gas-Filled Microbubbles: Ultrasound Contrast Agents for Targeted Molecular Imaging", Bioconjugate Chem., 2005, 16, 9-17.

Sato et al, "Direct Delivery of a Cytotoxic Anticancer Agent into the Metastatic Lymph Node Using Nana/Microbubbles and Ultrasound", PLOS One, Apr. 21, 2015.

Sato et al, "The combination of intralymphatic chemotherapy with ultrasound and nano-/microbubbles is efficient in the treatment of experimental tumors in mouse lymph nodes", Ultrasound in Med. & Biol., vol. 40, No. 6, pp. 1237-1249, 2014.

Deconti et al, "Clinical and Pharmacological Studies with cis-Diamminedichloroplatinum(II)", Cancer Research, vol. 33, pp. 1310-1315, Jun. 1973.

Holding et al, "Phase I trial of a cisplatin-albumin complex for the treatment of cancer on the head and neck", Br. J. clin. Pharmac. (1992), 33, 75-81.

Urien et al, "Population pharmacokinetics of total and unbound plasma cisplatin in adult patients", Br. J. Clin. Pharmacol., 57:6, 756-763, 2004.

(Continued)

*Primary Examiner* — Michael B. Pallay
(74) *Attorney, Agent, or Firm* — Fay Sharpe LLP

(57) ABSTRACT

Disclosed herein is a method for treating a cancer, the method includes following operations. A pharmaceutical composition is administered to a subject in need. The pharmaceutical composition includes a medium and a plurality of cisplatin-loaded microbubbles dispersed in the medium. Each cisplatin-loaded microbubble includes a shell portion and a core portion. The shell portion includes a plurality of albumin molecules and a plurality of first cisplatin molecules covalently bonding to the albumin molecules. The core portion is surrounded by the shell portion, wherein the core portion includes a mixture of inert gas and a plurality of second cisplatin molecules. Ultrasound energy is then applied to a tumor of the subject to break the cisplatin-loaded microbubbles.

30 Claims, 15 Drawing Sheets
(5 of 15 Drawing Sheet(s) Filed in Color)

(56) References Cited

OTHER PUBLICATIONS

Miyoshi et al, "Risk Factors Associated with Cisplatin-Induced Nephrotoxicity in Patients with Advanced Lung Cancer", Biol. Pharm. Bull. 39, vol. 39, No. 12, 2009-2014, 2016.

Yamamoto et al, "Multivariate analysis of risk factors for cisplatin-induced nephrotoxicity in gynecological cancer", J. Obstet. Gynaecol. Res. vol. 43, No. 12, 1880-1886, Dec. 2017.

Nanji et al., "Hyperuricemia and hypoalbuminemia predispose to cisplatin-induced nephrotoxicity", Cancer Chemother Pharmacol (1986) 17, 274-276.

Morris et al, "Fortification of blood plasma from cancer patients with human serum albumin decreases the concentration of cisplatin-derived toxic hydrolysis products in vitro", Royal Society of Chemistry, DOI: 10 1039/c4mt00220b.

Astolfi et al, "Coenzyme Q10 plus Multivitamin Treatment Prevents Cisplatin Ototoxicity in Rats", Plos One, DOI:10.1371/journal.pone.0162016, Sep. 15, 2016.

Chen et al, "Isonation of Systemically Delivered Cisplatin-Loaded Microbubbles Significantly Attenuates Nephrotoxicity of Chemotherapy in Experimental Models of Head and Neck Cancer", Cancers 2018, 10, 311, DOI:10.3390/cancers10090311.

Chen et al, "Supplementary Materials: Isonation of Systemically Delivered Cisplatin-Loaded Microbubbles Significantly Attenuates Nephrotoxicity of Chemotherapy in Experimental Models of Head and Neck Cancer", Cancers 2018, 10, 311.

Mayer, C.R. et al, "Ultrasound targeted microbubble destruction for drug and gene delivery." Expert Opin. Drug Deliv. 2008, 5, 1121-1138.

Ai-Ho Liao, et al., "Estimating the delivery efficiency of drug-loaded microbubbles in cancer cells with ultrasound and bioluminescence imaging", Ultrasound in Medicine & Biology, Jul. 18, 2012,pp. 1938-1948, vol. 38, No. 11, World Federation for Ultrasound in Medicine and Biology.

Kelsie F Timbie, et al., "MR image-guided delivery of cisplatin-loaded brain-penetrating nanoparticles to invasive glioma with focused ultrasound", Journal of Controlled Release, Mar. 11, 2017, pp. 120-131, vol. 263, Elsevier.

\* cited by examiner

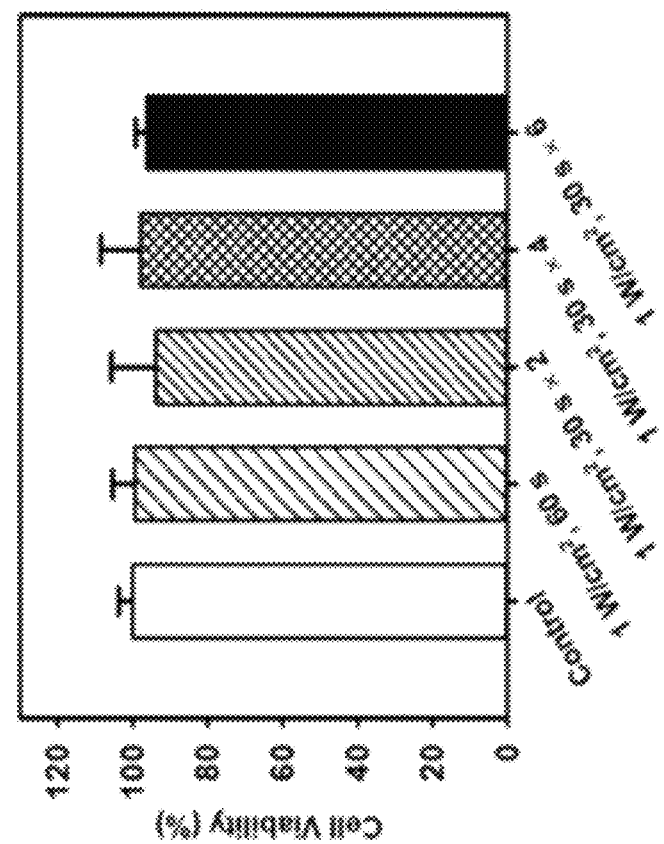
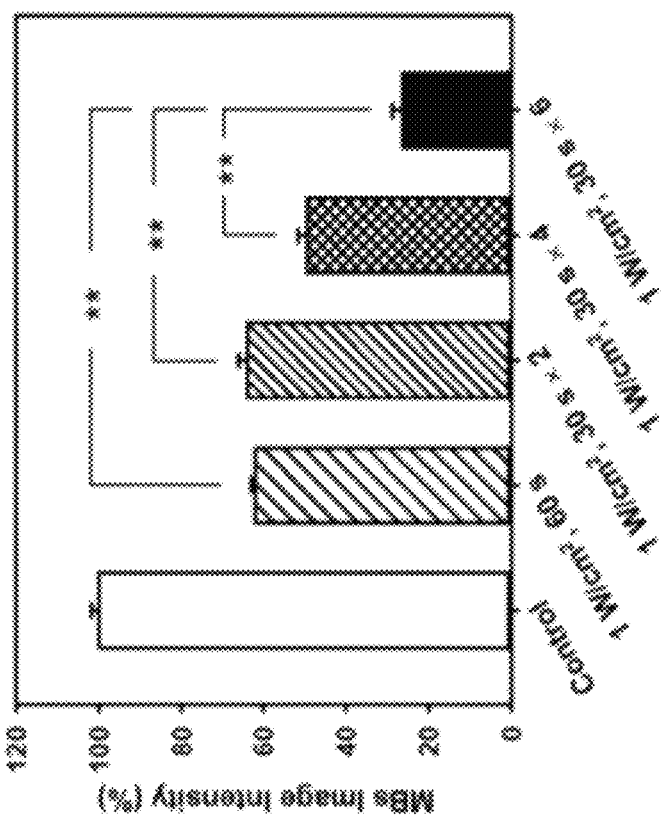
Fig. 6A
Fig. 6B

CISPLATIN-LOADED MICROBUBBLES, PHARMACEUTICAL COMPOSITION FOR TREATMENT OF CANCER, METHOD FOR PREPARING PHARMACEUTICAL COMPOSITIONS AND METHOD FOR TREATING CANCER

BACKGROUND

Field of Invention

The present invention relates to pharmaceutical compositions and methods for treatment of cancer. The present invention also relates to methods for preparing the pharmaceutical compositions.

Description of Related Art

For decades, ultrasound has been one of the most important tools in the medical or therapeutic field as it is an accurate, inexpensive and easily operated tool with no ionizing radiation. For the ultrasonic technology, the microbubble ultrasound contrast agent is applied intravascularly and the tiny bubbles of the microbubble ultrasound contrast agent in the blood vessel are excited by ultrasonic energy to generate harmonic resonance, which enhances the received ultrasound images. The application of the microbubble ultrasound contrast agents may help increase the contrast resolution and sensitivity of high-frequency ultrasound imaging.

Cis-Diamine platinum (II) Dichloride (CDDP), hereinafter referred to as "cisplatin", is one of the most common chemotherapy drugs for the treatment of head and neck cancer. Once cisplatin enters the cells, it is activated by water molecules to produce hydrolysis-dependent activation. When cisplatin inhibits cancer cells, it also kills healthy cells throughout the body, thereby causing undesirable side effects, especially nephrotoxicity. Therefore, the kidney damage caused by cisplatin remains the biggest challenge in clinical treatment.

SUMMARY

According to one aspect of the present disclosure, a cisplatin-loaded microbubble is provides. The cisplatin-loaded microbubble includes a shell portion and a core portion. The shell portion includes a plurality of albumin molecules and a plurality of first cisplatin molecules covalently bonded to the albumin molecules. The core portion is surrounded by the shell portion. The core portion includes a mixture of inert gas and a plurality of second cisplatin molecules.

According to one aspect of the present disclosure, a pharmaceutical composition for treatment of cancer is provided. The pharmaceutical composition for treatment of cancer includes a medium and a plurality of the cisplatin-loaded microbubbles dispersed in the medium. Each cisplatin-loaded microbubble includes a shell portion and a core portion surrounded by the shell portion. The shell portion includes a plurality of albumin molecules and a plurality of first cisplatin molecules covalently bonding to the albumin molecules. The core portion includes a mixture of inert gas and a plurality of second cisplatin molecules.

According to one aspect of the present disclosure, a method for preparing a pharmaceutical composition is provided. The method includes the operations described below. Albumin and cisplatin are mixed with saline to form a mixture, wherein the cisplatin is covalently bonded to the albumin. Inert gas is introduced and an ultrasonic oscillating treatment is applied to the mixture to form a plurality of cisplatin-loaded microbubbles therein. Each of the cisplatin-loaded microbubbles includes a shell portion and a core portion surrounded by the shell portion. The shell portion includes the albumin and a first portion of the cisplatin covalently bonded to the albumin molecules, and the core portion includes a mixture of inert gas and a second portion of the cisplatin.

According to one aspect of the present disclosure, a method for treating a cancer is provided. The method includes the operations described below. The pharmaceutical composition mentioned above is administered to a subject in need. Ultrasound energy is applied to a tumor of the subject to break the cisplatin-loaded microbubbles.

BRIEF DESCRIPTION OF THE DRAWINGS

The patent or application file contains at least one drawing/photograph executed in color. Copies of this patent with color drawing(s)/photograph(s) will be provided by the Office upon request and payment of the necessary fee.

The invention can be more fully understood by reading the following detailed description of the embodiment, with reference made to the accompanying drawings as follows:

FIG. 6A is a chart illustrating the relationship between the ultrasound exposure condition and the image intensity of the albumin microbubbles according to various examples.

FIG. 6B is a chart illustrating the relationship between the cell viability and the ultrasound exposures according to various examples.

DETAILED DESCRIPTION

Figure 1:
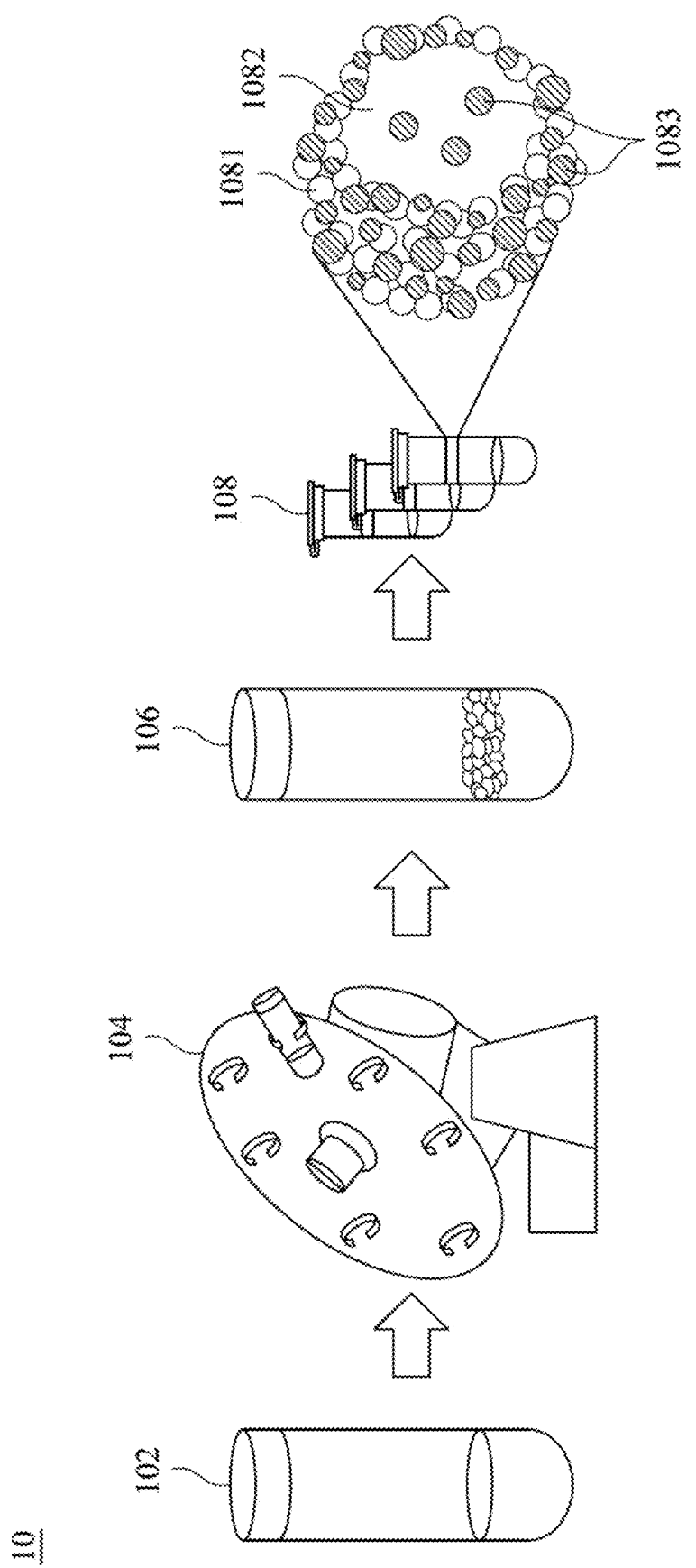
FIG. 1 is a diagram illustrating a method for preparing a pharmaceutical composition for treatment of cancer according to one embodiment of the present invention.

Reference will now be made in detail to the present embodiments of the invention, examples of which are illustrated in the accompanying drawings. Wherever possible, the same reference numbers are used in the drawings and the description to refer to the same or like parts.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The microbubble ultrasound contrast agent is mainly comprised of many small microbubbles with a size distribution of approximately 1 µm to 8 µm. The microbubble ultrasound contrast agent can be used to enhance the quality of ultrasonic images. Generally, the ideal microbubble ultrasound contrast agent has the following characteristics: (a) non-toxicity and can be metabolized; (b) can be injected into the living body's vein; (c) can pass through the pulmonary circulation and microcirculation; and (d) high stability. The microbubbles contained in the microbubble ultrasound contrast agent have stable shells and may be used to enhance the scattering signals of reflected ultrasound. Under various ultrasound energy intensities, using the microbubble ultrasound contrast agent can increase the penetration depth (i.e. absorption efficiency) and/or the amount of penetration (i.e. absorption) of the chemicals or small molecules at the applied area. According to the material of the microbubble's shell, the microbubble ultrasound contrast agent can be divided roughly into three categories: albumin microbubbles, liposome microbubbles or polymer microbubbles. In the present invention, protein as a matrix is used as an albumin microbubbles loading with anticancer drug.

One aspect of the present invention is to provide cisplatin-loaded albumin microbubbles. Particularly, the cisplatin-loaded albumin microbubbles may be used for treatment of cancer. According to various embodiments, each cisplatin-loaded albumin microbubble includes a shell portion and a core portion being surrounded by the shell portion. The shell portion includes a plurality of albumin molecules and a plurality of first cisplatin molecules covalently bonded to the albumin molecules. The core portion includes a mixture of inert gas and a plurality of second cisplatin molecules. In one embodiment, the core portion consists essentially of the inert gas and the second cisplatin molecules. In examples, the second cisplatin molecules are free of covalently bonding with the albumin molecules of the shell portion. In various embodiments, an average diameter of the cisplatin-loaded microbubbles ranges from about 0.6 µm to about 10 µm, for example 0.8 µm, 1 µm, 1.5 µm, 2 µm, 2.5 µm, 3 µm, 3.5 µm, 4 µm, 5 µm, and 8 µm. In one embodiment, an amount of the first cisplatin molecules is greater than an amount of the second cisplatin molecules. In various embodiments, the inert gas is selected from the group consisting of perfluoropropane ($C_3F_8$) gas, sulfur hexafluoride ($SF_6$) gas, and a combination thereof. The inert gas makes the overall structure of the microbubbles more stable and less susceptible to cracking.

Another aspect of the present invention is to provide a pharmaceutical composition for treatment of cancer. The pharmaceutical composition for treatment of cancer includes a medium and a plurality of the cisplatin-loaded microbubbles dispersed in the medium. Each microbubble includes a shell portion and a core portion surrounded by the shell portion. The shell portion includes a plurality of albumin molecules and a plurality of first cisplatin molecules covalently bonding to the albumin molecules. The core portion comprises a mixture of inert gas and a plurality of second cisplatin molecules. In some embodiments, the medium is capable of dissolving albumin and cisplatin. In some embodiments, the medium includes physiological saline. In one embodiment, the core portion consists essentially of the inert gas and the second cisplatin molecules. In some embodiments, the second cisplatin molecules are free of covalently bonding with the albumin molecules of the shell portion. In some embodiments, a weight ratio of the first cisplatin to the albumin molecules ranged from about 10 to about 25. For example, the weight ratio of the first cisplatin to the albumin molecules may be 11, 12, 13, 14 15, 16, 17, 18, 19, 20, 21, 22, 23, or 24. In some embodiments, the pharmaceutical composition for treatment of cancer has a cisplatin concentration ranged from about 250 µg/mL to about 450 µg/mL. For example, the cisplatin concentration may be 255, 265, 270, 275, 285, 295, 300, 305, 310, 315, 325, 335, 345, 355, 365, 375, 385, 395, 400, 405, 410, 415, 425, 435, 440, or 445 µg/mL. In some embodiments, an amount of the first cisplatin molecules is greater than an amount of the second cisplatin molecules. In some embodiments, the cisplatin-loaded microbubbles are present at a concentration ranged from $0.5-3\times10^8$ particles/mL in the pharmaceutical composition.

Yet another aspect of the present invention is to provide a method for preparing a pharmaceutical composition for treatment of cancer. FIG. 1 is a diagram schematically illustrating a method 10 for preparing the pharmaceutical composition for treatment of cancer according to some embodiments of the present invention. The method 10 for preparing the pharmaceutical composition includes operation 102, operation 104, operation 106, and operation 108.

In operation 102, albumin and cisplatin are mixed with saline to form a mixture. In operation 104, the mixture is placed on a mixer (such as for example a vortex mixer or the like) for incubating a suitable time period (such as for example 16 hours to 17 hours or other time periods, depending on the process conditions) such that the cisplatin is covalently bonded to the albumin. In some examples, the amount of the cisplatin is stoichiometrically greater than the amount of the albumin and therefore excess cisplatin is present in the mixture. In operation 106, inert gas is introduced and an ultrasonic oscillating treatment is applied to the mixture to form a plurality of cisplatin-loaded microbubbles therein. In operation 108, the mixture is centrifuged to form an upper foam layer including a plurality of the cisplatin-loaded microbubbles and liquid under the foam layer. In the foam layer, each of the cisplatin-loaded microbubbles includes a shell portion and a core portion surrounded by the shell portion. The shell portion includes the albumin and a first portion of the cisplatin covalently bonded to the albumin molecules, and the core portion includes a mixture of inert gas and a second portion of the cisplatin (e.g., excess cisplatin). According to one example, each cisplatin-loaded microbubble consists essentially of albumin 1081, inert gas 1082, and cisplatin 1083. However, in yet some examples, other anticancer drug may be added into the mixture and the added drug may be encapsulated in the microbubbles. After operation 108, a purification process may be performed to remove the "free" cisplatin which is neither bonded to the albumin nor encapsulated in the shell portion.

It will be appreciated that although the method 10 described above illustrates a number of operations, acts and/or features, not all of these operations, acts and/or features are necessarily required, and other un-illustrated operations, acts and/or features may also be present. For example, operation 104 described hereinbefore is optional, and may be replaced by any suitable mixing technique known in the art or even be omitted in some embodiments. Further, operation 108 is optional, and may be replaced by any suitable separation approach that separates the cisplatin-loaded microbubbles from the mixture. Also, the ordering of the operations and/or acts in some embodiments can vary from what is illustrated in these figures. In addition, the illustrated acts can be further divided into sub-acts in some implementations, while in other implementations some of the illustrated acts can be carried out concurrently with one another.

In some embodiments, the mixture has an albumin concentration ranged from 125-155 mg/ml and a cisplatin concentration ranged from 1-12 mg/ml. For example, the albumin concentration may be 126, 132, 140, 150, or 154 mg/ml, and the cisplatin concentration may be 2, 4, 6, 8, or 10 mg/ml. In some embodiments, the inert gas may be perfluoropropane ($C_3F_8$) gas, sulfur hexafluoride ($SF_6$) gas, or a combination of thereof. In some embodiments, the pharmaceutical composition for treatment of cancer consists essentially of the albumin, the cisplatin, the saline and the inert gas. In some embodiments, the cisplatin-loaded microbubbles have an averaged diameter ranged from about 0.6 μm to about 10 μm, for examples 1.02, 1.7, 2.05, 2.45, and 2.9 μm. In some embodiments, a concentration of the cisplatin-loaded microbubbles is ranged from about $0.1 \times 10^8$ to about $2.5 \times 10^8$ particles/ml or more in the pharmaceutical composition.

Yet another aspect of the present invention is to provide a method for treating cancer. The method includes the steps described below. The pharmaceutical composition for treatment of cancer as mentioned above is administered to a subject. Ultrasound energy is applied to a tumor of the subject to break the cisplatin-loaded microbubbles. In one embodiment, the method can be used for treating squamous cell cancer. For example, the method is used in the treatment of a wide range of other cancers, including lung, bladder, solid tumors of the head and neck, testes and ovarian cancers. In some embodiments, the ultrasound energy has a power of 1 W to 3 W. In some embodiments, the method further includes a step to measure the cisplatin concentration in a non-target tissue of the subject and/or the cisplatin concentration in the tissue of the tumor. In some embodiments, the cisplatin concentration of the non-target tissue is less than the cisplatin concentration of the tissue of the tumor. In various embodiments, the pharmaceutical composition for treatment of cancer has an albumin concentration ranged from about 580 mg/m$^2$ to about 7600 mg/m$^2$. For example, the albumin concentration may be 600, 800, 1000, 1500, 1800, 2000, 2200, 2500, 3000, 3500, 4000, 4500, 5000, 5500, 6000, 6500, 7000, 7200, or 7500 mg/m$^2$. In various embodiments, the pharmaceutical composition for treatment of cancer has a cisplatin concentration of about 50-650 mg/m$^2$. For example, the cisplatin concentration may be 60, 70, 80, 90, 100, 150, 170, 190, 200, 220, 240, 260, 280, 300, 310, 330, 350, 370, 390, 410, 420, 440, 460, 480, 500, 520, 550, 570, 600, 610, 620, 630, or 640 mg/m$^2$.

EXAMPLES

The examples below are used to illustrate some aspects of the present disclosure in details to enable a person skilled in the art to implement the present disclosure. The compared examples below are described to enable a person skilled in the art to more appreciate the present disclosure and the technical effect thereof. The examples and the compared examples herein are not intended to limit the present disclosure. The details of the examples are described in the following journal paper authored by the inventors of present disclosure: Chen, H.-K.; Zhang, S.-M.; Chang, J.-L.; Chen, H.-C.; Lin, Y.-C.; Shih, C.-P.; Sytwu, H.-K.; Fang, M.-C.; Lin, Y.-Y.; Kuo, C.-Y.; Liao, A.-H.; Chu, Y.-H.; Wang, C.-H. Insonation of Systemically Delivered Cisplatin-Loaded Microbubbles Significantly Attenuates Nephrotoxicity of Chemotherapy in Experimental Models of Head and Neck Cancer. *Cancers* 2018, 10, 311, which is herein incorporated by reference.

Example 1

The Optimal CDDP Concentration for High CDDP Loading Efficiency of the CDDP-Loaded MBs Several cisplatin concentrations were tried out to determine a relatively optimal CDDP concentration in pursuit of a high CDDP loading efficiency of the CDDP-HSA. Pharmaceutical compositions 1-5 listed in table 1 below were prepared. The experiments of the pharmaceutical compositions 1-5 were carried out in the same manner, except that the CDDP concentrations were different. The parameters of pharmaceutical compositions 1-5 are listed in table 1 below.

TABLE 1

|  | Pharmaceutical composition | | | | |
| --- | --- | --- | --- | --- | --- |
|  | 1 | 2 | 3 | 4 | 5 |
| Cisplatin Concentration (mg/mL) | 1 | 2 | 4 | 6 | 12 |
| Albumin Concentration (mg/mL) | 140 | 140 | 140 | 140 | 140 |

In pharmaceutical composition 1, as a descriptive example, 1 mg/mL cisplatin (Sigma-Aldrich, St. Louis, Mo., USA) in 2 ml saline was mixed with 140 mg/mL human serum albumin solution (Octapharma, Vienna, Austria) to form a mixture. The mixture was then incubated in the dark at 37° C., and placed on a vortex mixer (30 rpm) for 17 hours. Saline was then added to the mixture to make 10 mL in volume. Perfluorocarbon ($C_3F_8$) gas was introduced and an ultrasonic oscillating treatment using a sonicator (Branson Ultrasonics Co., Danbury, Conn., USA) was applied to the mixture for a period of 90 seconds. The mixture was then centrifuged in 1 mL aliquots at 1200 rpm for 2 min (Thermo Fisher Science, Bremen, Germany) to form an upper foam layer including a plurality of the cisplatin-loaded microbubbles (CDDP-loaded MBs) and liquid layer under the foam layer. The lower liquid layer was removed and 1 mL of physiological saline (pH 7.4, 0.9% sodium chloride) was added for re-centrifugation. These steps were repeated three times to eliminate the free (unbound) cisplatin. Aliquots of the CDDP-MBs were stored at 4° C.

Figure 2:
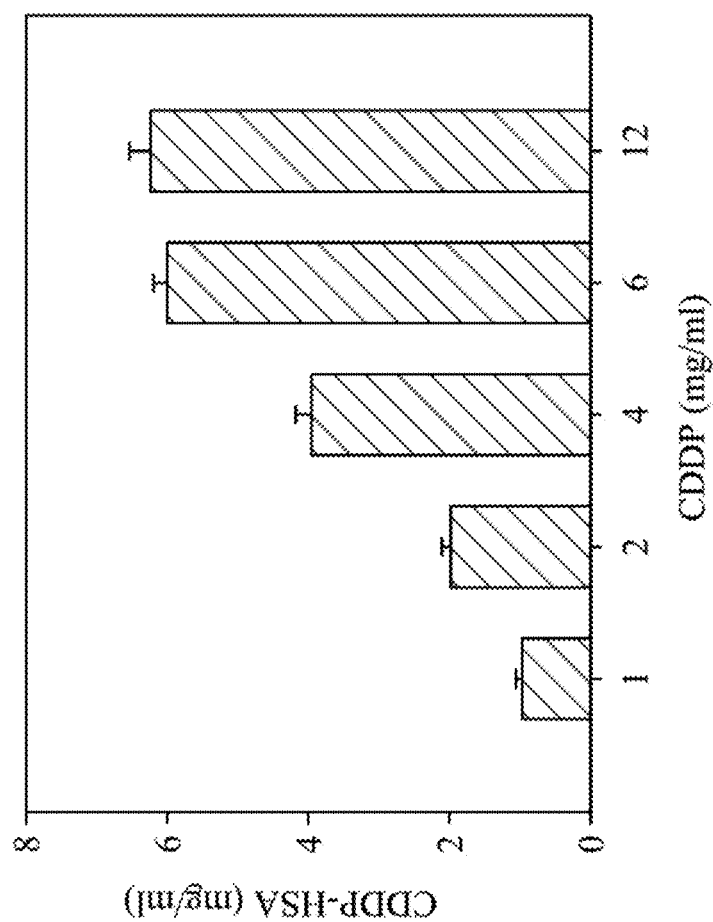
FIG. 2 is a diagram showing the loading efficiency of pharmaceutical compositions 1-5 in Example 1.

FIG. 2 is a diagram showing the loading efficiency of pharmaceutical compositions 1-5. The loading efficiencies of the cisplatin molecules in the present disclosure were calculated by taking the cisplatin amount loaded on albumin microbubbles divided by the cisplatin amount initially used in the preparation of the pharmaceutical composition. As shown in FIG. 2, no significant difference was noted between 6 mg/mL (pharmaceutical composition 4) and 12 mg/mL (pharmaceutical composition 5). Therefore, cisplatin concentration of 6 mg/mL (pharmaceutical composition 4) was used for the preparation of the pharmaceutical composition in the subsequent examples.

Example 2

The Optimal Albumin Concentration for High CDDP Loading Efficiency of the CDDP-Loaded MBs In Example 2, several albumin concentrations were tried out to determine a relatively optimal albumin concentration in pursuit of a high CDDP loading efficiency of the CDDP-loaded microbubbles (MBs). Pharmaceutical compositions 4, 6, 7 and comparative example 1 listed in Table 2 below were prepared. The experiments of the pharmaceutical compositions 6 and 7 were carried out in the same manner as pharmaceutical composition 4, except the albumin concentrations were different. The composition, diameter, number, and cisplatin loading efficiency of cisplatin-loaded microbubbles for each experiment group are listed in Table 2 below.

Figure 3B:
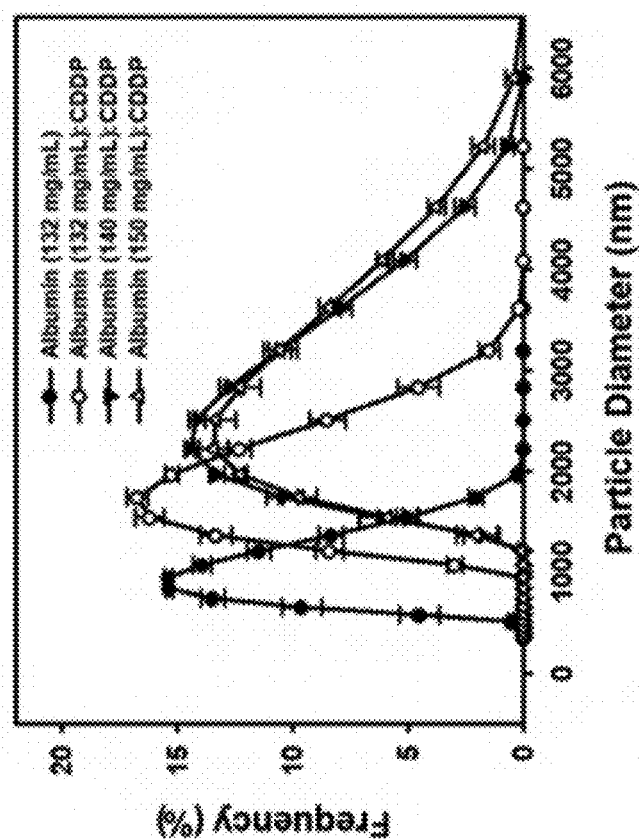
FIG. 3B is a chart illustrating the relationship between frequency and microbubble diameter according to various examples.
Figure 3A:
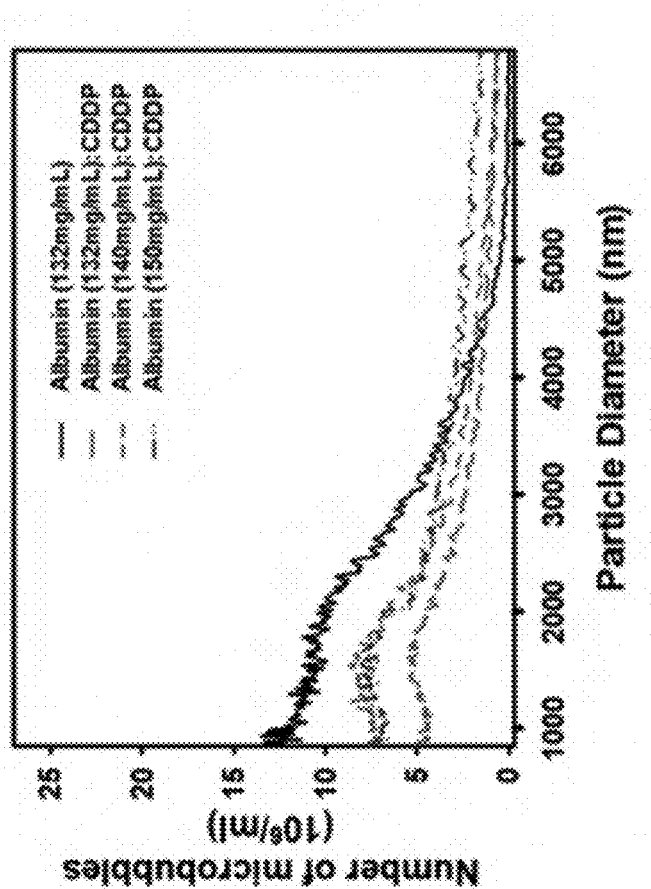
FIG. 3A is a chart illustrating the relationship between numbers of microbubbles and microbubble diameter according to various examples.

FIG. 3A is a chart illustrating the relationship between numbers of microbubbles and microbubble diameter associated with Example 2. FIG. 3B is a chart illustrating the relationship between the frequency and microbubble diameters of Example 2. The size distribution of CDDP-MBs in the solution was measured by dynamic light scattering (Nanoparticle Analyzer, Horiba, Kyoto, Japan), and the bubble number was measured with a MultiSizer III device (Beckman Coulter, Fullerton, Calif., USA) using a 30-μm aperture probe with a measurement boundary ranging from 0.6 to 10 μm.

As shown in Table 2 and FIGS. 3A-3B, the average size and concentration of albumin microbubbles without cisplatin (comparative example 1) was 1.02±0.11 μm and 1.40±2.22×$10^8$ particles/mL, respectively. However, referring to pharmaceutical composition 6, the microbubble concentration would drop to about 50% of its initial value (i.e., comparative example 1) when the cisplatin concentration of 6 mg/mL was used. Compared with pharmaceutical compositions 4 and 6, increasing the concentration of albumin from 132 mg/mL to 140 mg/mL, both the cisplatin loading efficiency and the microbubble concentration were increased to 10.09±0.23% and 1.09±1.31×$10^8$ particles/mL, respectively. Further increasing the concentration of albumin up to 150 mg/mL (pharmaceutical composition 7) led to a significant decrease in the loading efficiency to a level of 7.70±1.21%. Therefore, pharmaceutical composition 4 (albumin concentration of 140 mg/mL and cisplatin concentration of 6 mg/mL) was used for preparation for cisplatin-loaded albumin microbubbles in the subsequent examples.

Figure 4A:
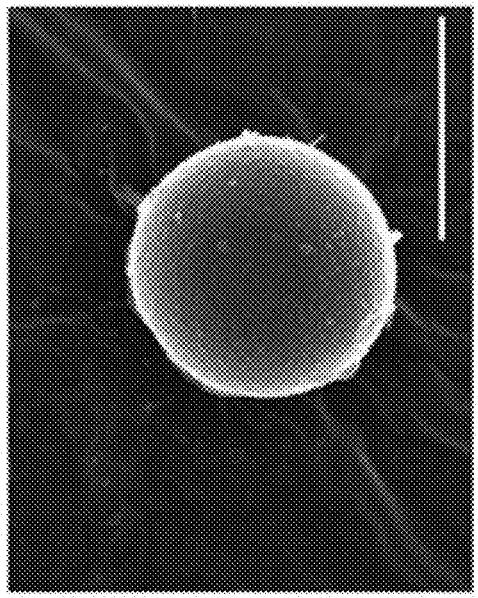
FIG. 4A and FIG. 4B are respectively light microscopy and scanning electron microscopy images according to comparative example.
Figure 4B:
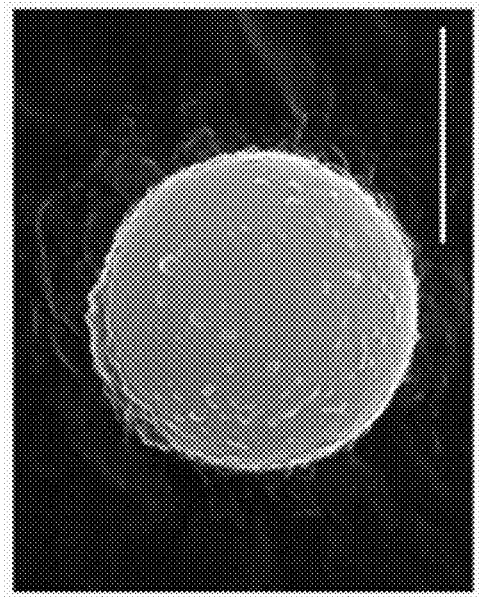
Figure 4C:
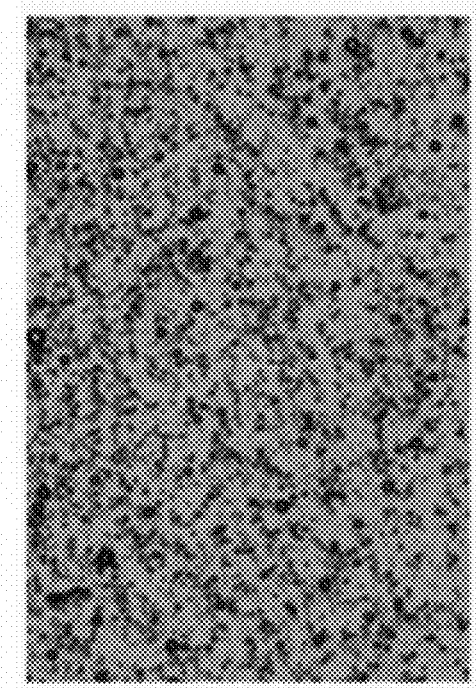
FIG. 4C and FIG. 4D are respectively light microscopy and scanning electron microscopy images according to one example.
Figure 4D:
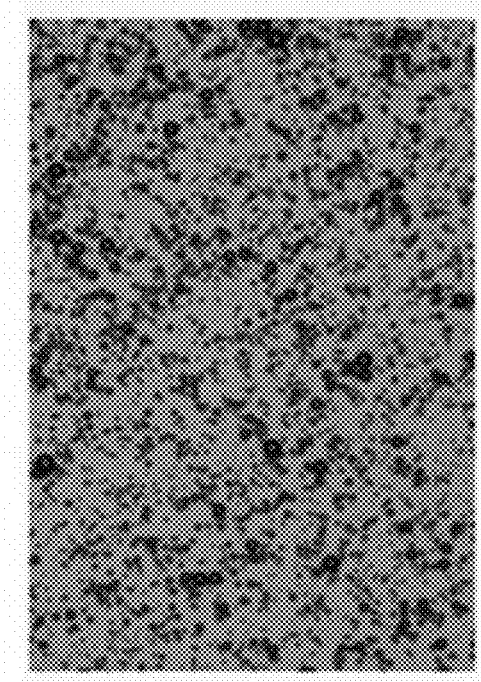

FIG. 4A and FIG. 4B are respectively light microscopy and scanning electron microscopy images according to comparative example 1. FIG. 4C and FIG. 4D are respectively light microscopy and scanning electron microscopy images according to pharmaceutical composition 4.

Examples 3-6

The Ultrasound Exposure Parameters for Microbubbles Destruction In Vitro

Several parameters of the ultrasound exposure were examined in order to obtain relatively optimal ultrasound exposure parameters for microbubbles destruction in vitro. In Examples 3-6, the acoustic intensity were 1 W/$cm^2$, and the ultrasound exposure time and cycles of ultrasound operations were studied, which are listed in Table 3 below.

TABLE 2

|  | Comparative example 1 | Pharmaceutical Composition 4 | Pharmaceutical Composition 6 | Pharmaceutical Composition 7 |
| --- | --- | --- | --- | --- |
| Albumin Concentration (mg/mL) | 132 | 140 | 132 | 150 |
| Cisplatin Concentration (mg/mL) | — | 6 | 6 | 6 |
| Cisplatin content of pharmaceutical composition (μg/mL) | — | 403.5 ± 4.52 | 391.3 ± 4.25 | 308 ± 24.3 |
| Cisplatin loading efficiency (%) | — | 10.09 ± 0.23 | 9.78 ± 0.25 | 7.70 ± 1.21 |
| Microbubble Diameter (μm) | 1.02 ± 0.11 | 2.05 ± 0.61 | 1.70 ± 0.73 | 2.45 ± 0.45 |
| Microbubble concentration (×$10^8$ bubbles/mL) | 1.40 ± 2.22 | 1.09 ± 1.31 | 0.71 ± 0.56 | 1.05 ± 0.36 |

TABLE 3

| | Comparative example 2 | Example 3 | Example 4 | Example 5 | Example 6 |
|---|---|---|---|---|---|
| Acoustic intensity (W/cm$^2$) | — | 1 | 1 | 1 | 1 |
| exposure time (second) | — | 60 | 30 | 30 | 30 |
| cycles | — | 1 | 2 | 4 | 6 |
| Destruction degree (%) | 0 | 37 | 36.1 | 50.4 | 73.7 |

Figure 5:
FIG. 5 is a microbubble destruction diagram using different ultrasound exposure parameter according to various examples.

FIG. 5 is a series of image photos showing the albumin microbubble destruction by using different ultrasound exposure parameters in examples 3-6 and comparative example 2. FIG. 6A is a chart illustrating the relationship between the ultrasound exposure condition and the image intensity of the albumin microbubbles, which were obtained from MATLAB program process. As illustrated in Table 3 and FIG. 6A, the destruction degrees of the albumin microbubbles were 36.1%, 50.4%, and 73.7% respectively in Examples 4, 5 and 6.

FIG. 6B is a chart illustrating the relationship between the cell viability and the ultrasound exposures in comparative example 2 and examples 3-6. As shown in FIG. 6B, at an acoustic intensity of 1 W/cm$^2$, an ultrasound exposure of 30 seconds for 6 cycles did not affect the viability of ATCC HTB-43 (FaDu) cells in culture. Consequently, the ultrasound exposure of 30 seconds for 6 cycles was used for subsequent examples in vitro.

Example 7

ATCC HTB-43 (FaDu) Cell Cytotoxicity Assay Experiments In Vitro

In Example 7, the cytotoxicity of different forms of cisplatin were studied, i.e., cisplatin in saline, cisplatin covalently loaded on albumin microbubbles in saline, and cisplatin simply mixed with albumin microbubbles in saline (i.e., cisplatin is not covalently bounded to albumin microbubbles). Each of the cisplatin forms had been prepared and experimented at different cisplatin concentrations of 1 μM, 5 μM, and 10 μM. Particularly, 2×10$^4$ FaDu cells/well in 24-well plates were treated by different forms of cisplatin at different cisplatin concentrations. Furthermore, each of the cisplatin forms had been experimented with or without ultrasound exposure. The various experimental conditions are listed in table 4 below. Ultrasonic treatments were not used in conditions 1, 3 and 5, while ultrasonic treatments were used (1 W/cm$^2$, 30 seconds for 6 cycles) in conditions 2, 4 and 6.

TABLE 4

| | Condition | | | | | |
|---|---|---|---|---|---|---|
| | 1 | 2 | 3 | 4 | 5 | 6 |
| Cisplatin in saline | V | V | — | — | — | — |
| Mixture of albumin microbubbles and cisplatin | — | — | V | V | — | — |
| Cisplatin covalently loaded on albumin microbubbles | — | — | — | — | V | V |
| Ultrasound treatment | — | V | — | V | — | V |

Figure 7B:
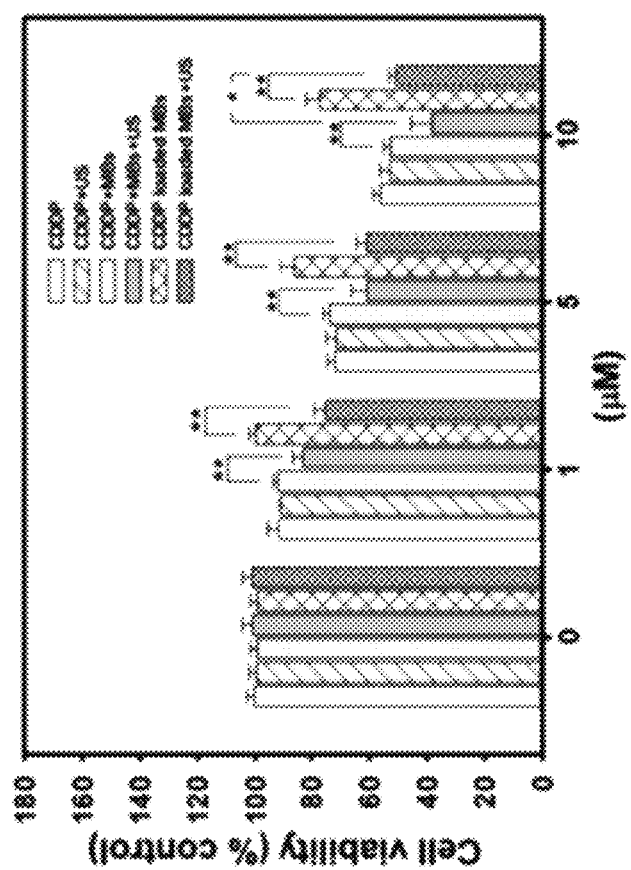
FIG. 7B is a chart showing the comparison of cell viability between different forms of cisplatin at different cisplatin concentrations according to various examples.
Figure 7A:
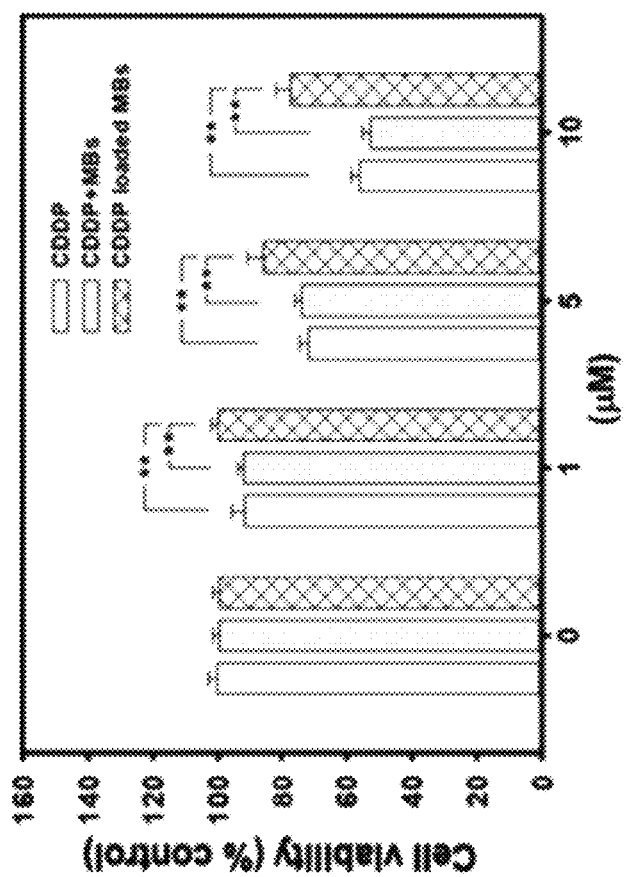
FIG. 7A is a chart showing the comparison of cell viability between different forms of cisplatin at different cisplatin concentrations according to various examples.

FIG. 7A is a chart showing the comparison of cell viability between different forms of cisplatin (i.e., conditions 1, 3, and 5) at different cisplatin concentrations. In FIG. 7A, the symbol "CDDP" represents cisplatin in saline, the symbol "CDDP+MBs" represents cisplatin simply mixed with albumin microbubbles, and the symbol "CDDP loaded MBs" represents cisplatin covalently loaded on albumin microbubbles. As shown in FIG. 7A, among these concentrations, the condition 3 (i.e., CDDP+MBs) shows no significant increase in toxicity as compared with condition 1 (i.e., CDDP). Nevertheless, condition 5 (i.e., CDDP loaded on MBs) shows a significantly lower toxic response than condition 1 or condition 3 at any concentration. These experiments suggest that additional administration of albumin microbubbles did not interfere in the cisplatin activity, but cisplatin loaded onto albumin microbubbles shows a significant reduction in cytotoxicity.

FIG. 7B is a chart showing the comparison of cell viability between different forms of cisplatin (i.e., conditions 1-6) at different cisplatin concentrations. As shown in FIG. 7A, the symbol "+US" represents the ultrasonic treatment being performed. Interestingly, when MBs were co-administered, the toxicity of CDDP was markedly enhanced after ultrasonic treatment was performed. See "CDDP+MBs+US" vs. "CDDP+MB"; and "CDDP loaded MBs+US" vs. "CDDP loaded MBs". As compared the results of conditions 1-2 with conditions 3-4 where the albumin microbubbles are simply mixed with cisplatin, it reveals that the presence of albumin microbubbles and ultrasound collectively together with cisplatin unpredictably enhance the cytotoxicity of cisplatin. This implies that the cellular sensitivity to or uptake of cisplatin is unexpectedly enhanced. In comparison of condition 3-4 with conditions 5-6, when cisplatin is loaded onto albumin microbubbles, the cytotoxicity prior to the ultrasonic treatment is much less, but the cytotoxicity after ultrasonic treatments is comparable to that of condition 3-4.

Examples 8-10

The Ultrasound Parameters Experiment In Vivo

In Examples 8-10, suitable ultrasound parameters (such as power or intensity) were studied in vivo by testing different settings of acoustic intensity in tissue-mimicking agarose phantoms. The testing conditions and experimental results are listed in Table 5.

TABLE 5

| | Example 8 | Example 9 | Example 10 |
|---|---|---|---|
| Acoustic intensity (W/cm$^2$) | 1 | 2 | 3 |
| Exposure time (second) | 30 | 30 | 30 |
| Destruction efficiency (%) | 24.39 ± 0.46 | 54.74 ± 0.1 | 79.6 ± 0.64 |

Figure 8:
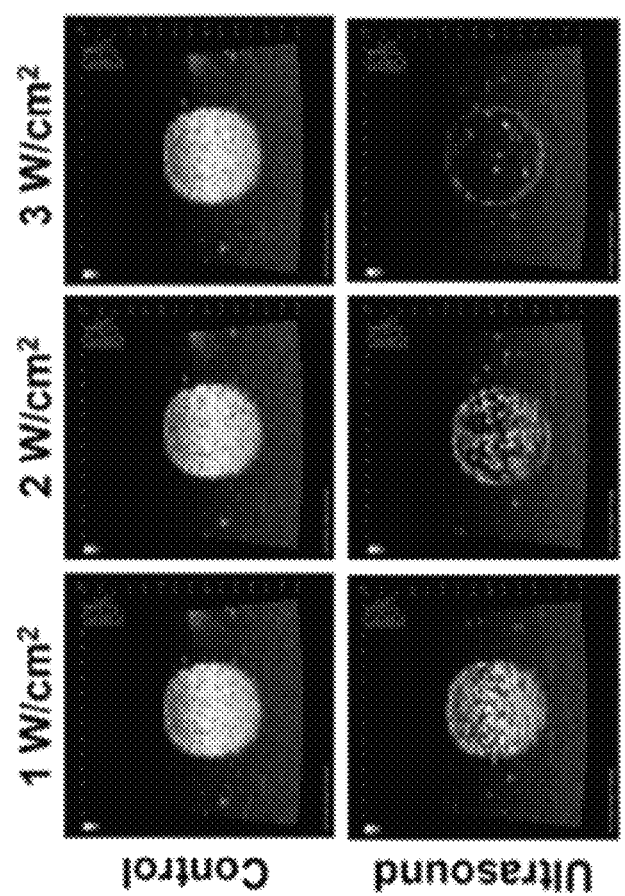
FIG. 8 is high frequency ultrasound images of albumin microbubbles in tissue-mimicking agarose phantoms under different ultrasound intensity according to various examples.

FIG. 8 is high frequency ultrasound images of albumin microbubbles in tissue-mimicking agarose phantoms under different ultrasound intensity in Examples 8-10. As shown in Table 5 and FIG. 8, the destruction efficiencies of the albumin microbubbles at acoustic intensities of 1 $W/cm^2$, 2 $W/cm^2$, and 3 $W/cm^2$ for 30 seconds were respectively 24.39±0.46%, 54.74±0.1%, and 79.6±0.64%. Therefore, the power and exposure time of ultrasound were set at 3 $W/cm^2$ and 30 seconds in all subsequent experiments in vivo.

Example 11

Influence of Microbubbles and Ultrasound on the Cisplatin Accumulation In Vivo

Figure 9A:
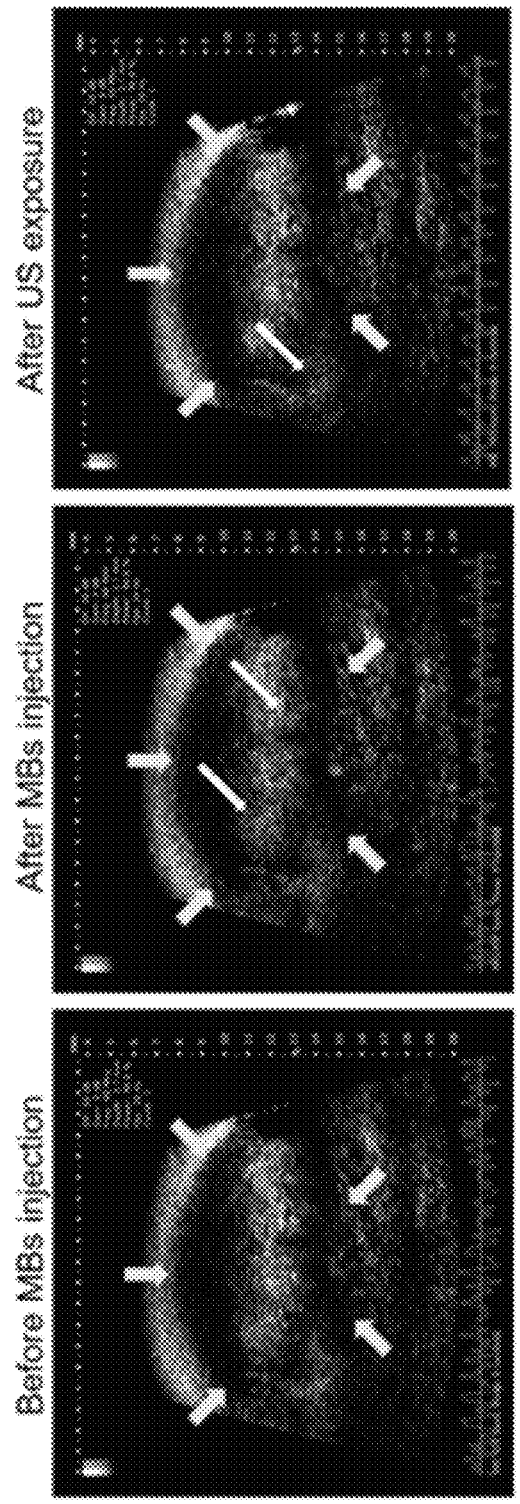
FIG. 9A is a series of high frequency ultrasound images focuses on head and neck carcinoma tumor lesions according to one example.

FIG. 9A is a series of high frequency ultrasound images focuses on head and neck carcinoma tumor lesions (yellow arrows). FIG. 9A demonstrates the real time appearance of albumin microbubbles (green dots) within the tumor (white arrows) after mouse tail vein microbubble injection, followed by the ultrasonic application (with a power setting of 3 $W/cm^2$) to the tumor site for 30 seconds in order to destruct the microbubbles. It was observed that the microbubbles subsequently disappeared after ultrasound was applied. These images shows that intravenous injected microbubbles circulated to the tumor lesions, where the microbubbles were destructed by the applied ultrasound, thereby releasing cisplatin from the cisplatin-loaded albumin microbubbles.

Figure 9B:
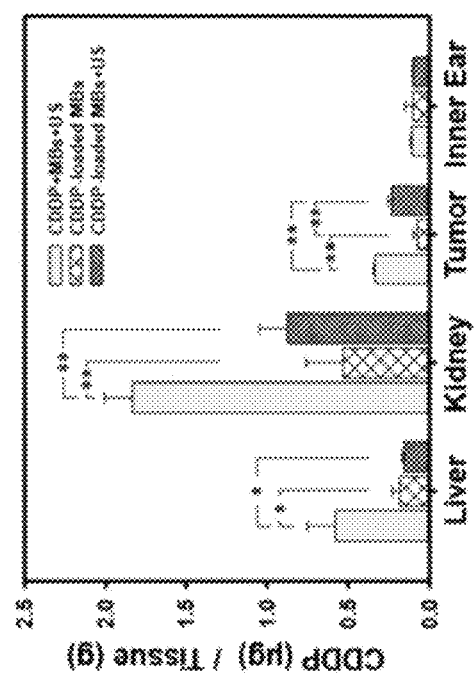
FIG. 9B is a chart illustrating the systemic biodistribution of cisplatin to relevant organs according to various examples.

FIG. 9B shows the systemic biodistribution of cisplatin to relevant organs 20 min after administration of various cisplatin-related chemotherapy treatments using the compositions described in conditions 4-6 of Example 7. The cisplatin concentration in tissues of different organs was determined by using inductively coupled plasma mass spectrometry (ICP-MS) quantitative method. As shown, the kidney accumulated the greatest amount of cisplatin among the organs investigated, followed by the liver and then the inner ear. Both the cisplatin-loaded albumin microbubbles and cisplatin-loaded albumin microbubbles with the ultrasound treatments significantly decreased the cisplatin uptake in the kidney and liver when compared with cisplatin administration alone. The results suggest that conjugation (e.g., covalently bonding) of cisplatin with albumin microbubbles significantly reduces its systemic toxicity, which were consistent with the in vitro experimental results in FaDu cells (Example 7). In addition, no significant treatment differences were noted for the inner ear. The cisplatin level in tumors after the ultrasound treatment (cisplatin=0.34±0.07 μg/tissue (g)) is at least 3 folds of that prior to the ultrasound treatment (cisplatin=0.09±0.03 μg/tissue (g)).

Example 12

The Anti-Tumor Effect of Cisplatin-Based Chemotherapy Evaluated In Vivo on the Growth of Head and Neck Cancer Severe combined immunodeficiency (SCID) mice were subcutaneously implanted with luminescence-labelled hypopharynx carcinoma cell line (FaDu-fLuc/GFP) ($2 \times 10^6$ cells/mouse) into the right flank region on Day 0. On Day 4, tumor xenograft formation and size in implanted SCID mice were determined by IVIS® bioluminescence imaging system (version 4.4, Caliper Life Sciences, Alameda, Calif., USA). The implanted SCID mice were then classified into group I to group V (hereinafter referred to as "Gps I-V"), and the implanted SCID mice of each group were treated with different pharmaceutical compositions, which are summarized in Table 6 below. Specifically, the mice of Gp I was the control group, and was treated with saline. The mice of Gp II were treated with cisplatin dissolved in saline. The mice of Gp III were treated with saline containing the mixture of cisplatin and albumin microbubbles (concentration: $1.4 \times 10^8$ particles/mL), followed by ultrasound exposure (power: 3 $W/cm^2$, 30 seconds). The mice of Gp IV were treated with saline containing cisplatin-loaded albumin microbubbles (concentration: $1.4 \times 10^8$ particles/mL), without ultrasound exposure. The mice of Gp V were treated with saline containing cisplatin-loaded albumin microbubbles (concentration: $1.4 \times 10^8$ particles/mL), followed by ultrasound exposure (power: 3 $W/cm^2$, 30 seconds). All medications, i.e., saline, cisplatin, the mixture of cisplatin and albumin microbubbles and cisplatin-loaded albumin microbubbles, were given by intravenous injection in a volume of 100 μL via the tail vein on Days 4, 7, 11, 14, 17, 20, 23, 26, and 30. For Gp III and Gp V, after injection, the ultrasound probe was applied to the tumors for 30 seconds with jelly being placed between the probe and the tumor. The anti-tumor effect of cisplatin-based chemotherapy was evaluated in vivo on the growth of head and neck cancer by twice-weekly recordings of luciferase bioluminescence data derived from IVIS® images. On day 33, after the IVIS® images of the mice were obtained, the mice were sacrificed and analysed.

TABLE 6

Figure 10A:
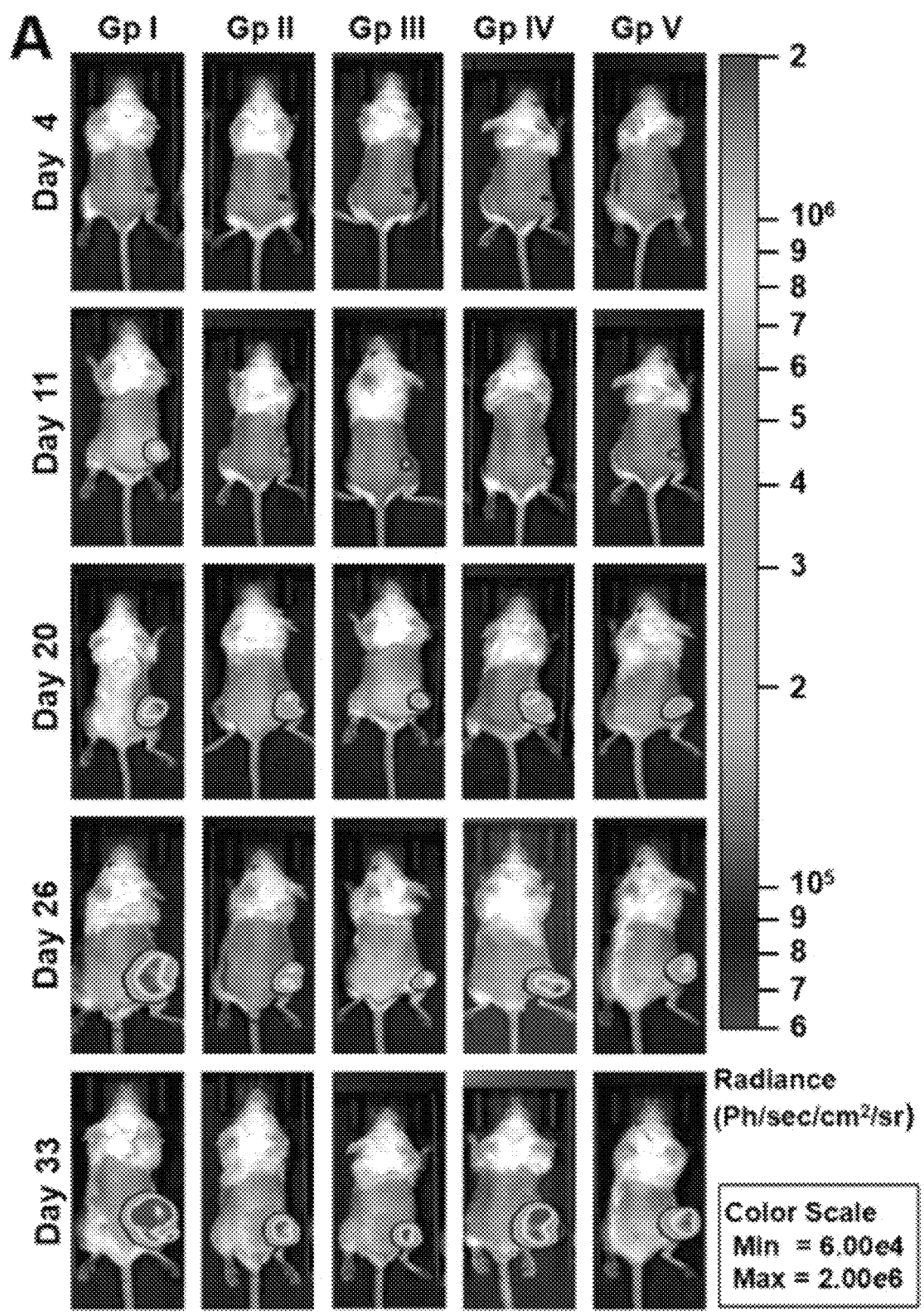
FIG. 10A is a series of IVIS® images showing tumor growth and chemotherapy results of living mice according to some examples.
Figure 10B:
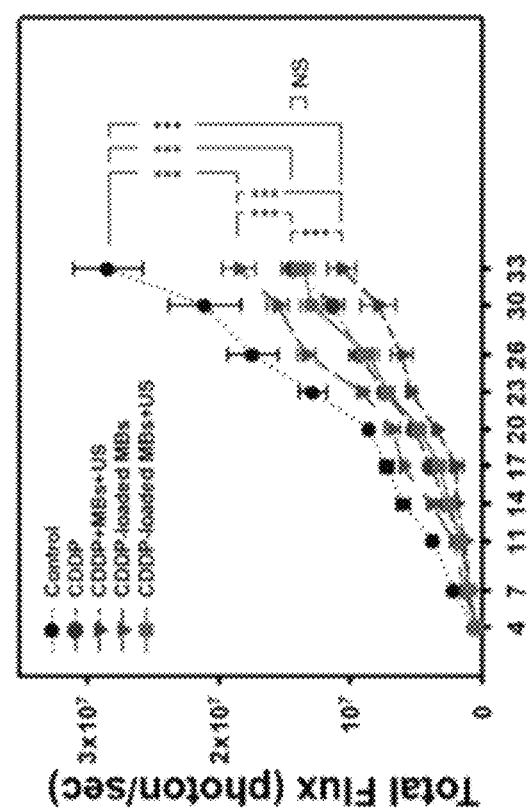
FIG. 10B is a chart illustrating the relationship between luminescence flux value and days of treatment obtained from the IVIS® images of FIG. 10A.
Figure 10C:
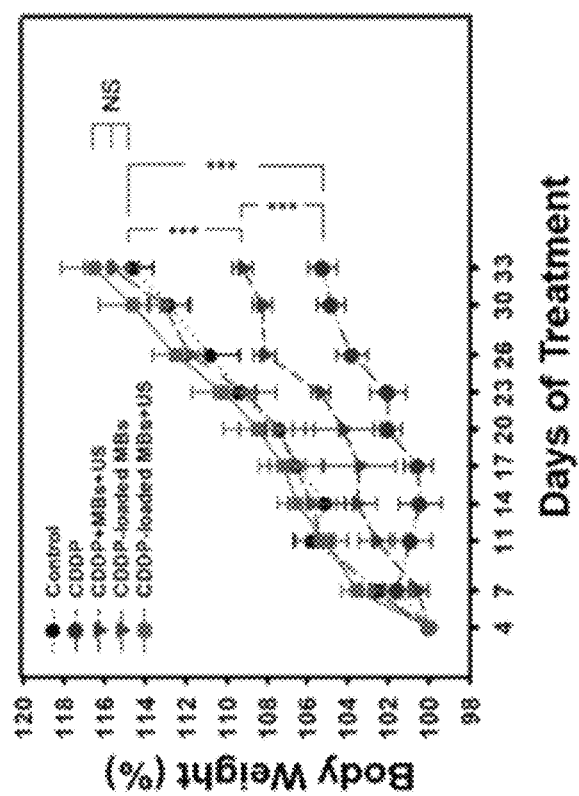
FIG. 10C is a chart illustrating the relationship between the body weight and days of treatment in the scheme of animal study design according to one example.

| Group | Pharmaceutical compositions | Symbol in FIGS. 10B and 10C |
|---|---|---|
| Gp I | saline | Control |
| Gp II | cisplatin dissolved in saline | CDDP |
| Gp III | saline containing the mixture of cisplatin and albumin microbubbles, followed by ultrasound exposure | CDDP + MBs + US |
| Gp IV | saline containing cisplatin-loaded albumin microbubbles, without ultrasound exposure | CDDP-loaded MBs |
| Gp V | saline containing cisplatin-loaded albumin microbubbles, followed by ultrasound exposure | CDDP-loaded MBs + US |

FIG. 10A is a series of IVIS® images showing tumor growth and chemotherapy results of living mice of Gps I-V from day 4 to day 33. FIG. 10B is a chart illustrating the relationship between luminescence flux value and days of treatment obtained from the IVIS® images of FIG. 10A. Referring to FIG. 10A and FIG. 10B, on Day 33, after chemotherapy, Gps II-V showed significant suppression of tumor growth as compared to the Gp I, with 30-65% reduction in tumor growth. Tumor reduction between Gp II ("CDDP") and Gp V ("CDDP-loaded MBs+US") did not show considerable difference; however, they all displayed significantly better outcomes as compared to Gp IV ("CDDP-loaded MBs"). Gp III ("CDDP+MBs+US") achieved the best inhibition of tumor growth among all treatments. Gp III gave significantly better outcomes than Gp II (treated with cisplatin alone) or Gp V (treated with cisplatin-loaded albumin microbubbles plus ultrasound), indicating that the cooperation of albumin microbubbles with ultrasound can additively enhance the uptake of cisplatin by head and neck cancer cells in vivo.

FIG. 10C is a chart illustrating the relationship between the body weight and days of treatment associated with the mice of Gps I-V. As shown in FIG. 10C, during the 33-day treatment period, although all animals showed different degrees of gain in body weight (BW), Gp II and Gp III treatments both showed statistically smaller body weight gain when compared with Gp I, Gp IV, and Gp V treatments. The higher body weight gain in Gp III compared with Gp II implies that the addition of albumin microbubbles may have a positive effect on the gain of body weight during cisplatin chemotherapy.

Example 13

Figure 11A:
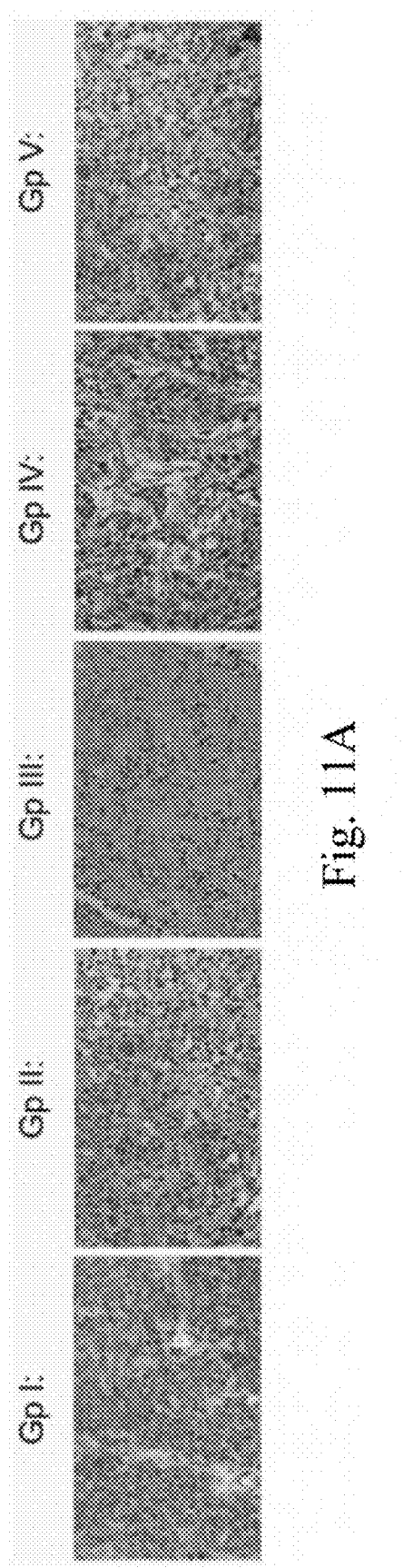
FIG. 11A and FIG. 11B are 400-fold magnification images showing the H&E-staining and TUNEL sections of tumor site lesions respectively according to various examples.
Figure 11B:
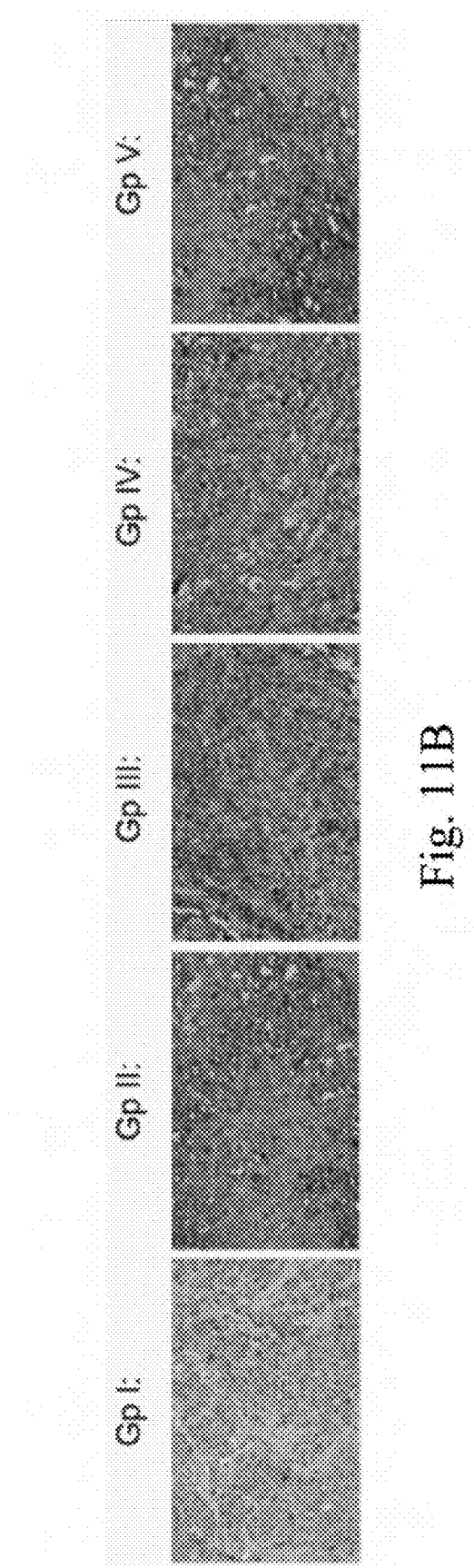

Effects of Various Cisplatin-Loaded Chemotherapies on Cell Death in Target Tumor Tissues and Non-Target Kidney Parenchyma The histopathological examination was carried out to investigate the impact of cisplatin-based chemotherapies on the tumor and kidney tissues of the mice of Gps I-V at Day 33 in Example 12. FaDu xenografted tumors and kidneys of SCID mice of Gps I-V were removed for histological examination. Xenografted tumors were examined by H&E staining and TUNEL assays. FIG. 11A and FIG. 11B respectively show the images (original magnification ×400) of H&E staining assay and TUNEL assay of Gps I-V. The H&E-stained sections of tumor lesions showed that cancer cells exhibited a nest-like distribution and disordered arrangement. In the control group, tumor cells were closely arranged with complete and atypical structures. By contrast, the chemotherapy groups showed more tumor cell apoptosis, characterized by incomplete cell membranes, condensed cytoplasm, pyknotic or cracking nuclei, and cavity-shaped organization. Significantly, the degree and extent of tumor cell apoptosis assessed by TUNEL staining among Gp I-V was consistent with the result of tumor reduction shown in FIG. 10A. Particularly, Gp III (CDDP+MBs+US) showed the greatest amount of apoptosis, whereas Group IV (CDDP-loaded MBs) showed less apoptosis. Both the CDDP (Group II) and CDDP-MBs+US (Group V) treatments showed similar TUNEL positive staining. These results suggest that CDDP, when delivered in a form bound with MBs and exposed to ultrasound, can achieve a tumor killing effect similar to that achieved with CDDP alone.

Figure 11C:
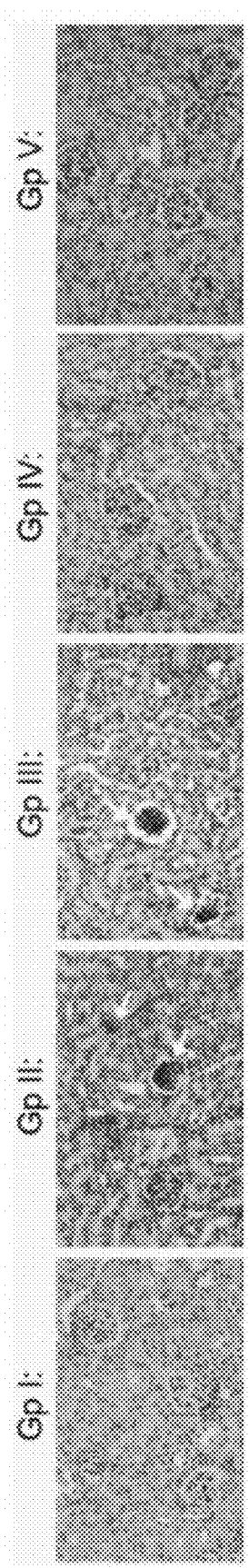
FIG. 11C is 400-fold magnification images showing sections of the kidney glomeruli site lesions respectively according to various examples.
Figure 11D:
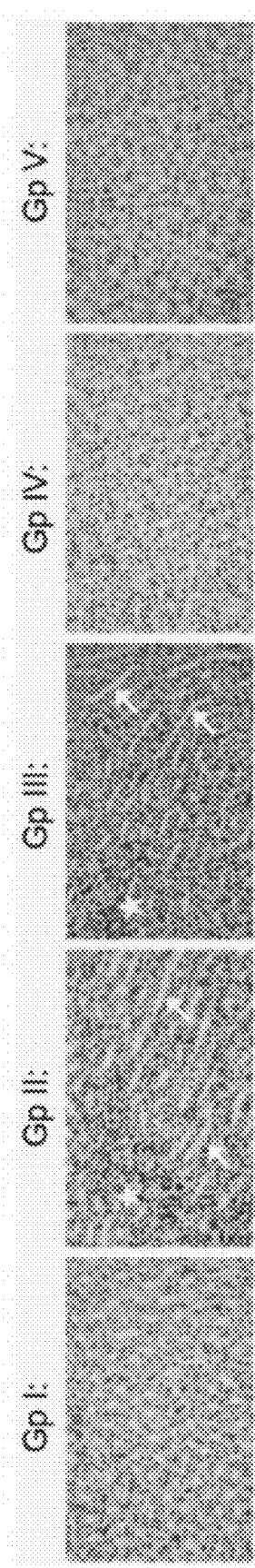
FIG. 11D is 400-fold magnification images showing sections of the kidney tubules site lesions respectively according to various examples.

FIG. 11C and FIG. 11D respectively show the images (original magnification ×400) of kidney glomeruli and kidney tubules of Gps I-V. The systemic cytotoxicity of CDDP chemotherapy in the non-target kidney tissue showed that CDDP treatment resulted in notable histological changes in the renal parenchyma, as indicated by vacuolation, or even atrophy, of the endothelium lining the glomerular tufts (FIG. 11C) and necrosis and vacuolation of the epithelial lining and cystic dilation of the renal tubules (FIG. 11D). Marked cytotoxic histological changes were noted in the kidneys of groups administered CDDP alone (Gp II) or co-administered CDDP and MBs (Gp III); however, these changes were attenuated in groups treated with CDDP-loaded MBs (Gp IV) or CDDP-loaded MBs+US (Gp V). In addition, the kidney weight ratios (expressed as a percentage of kidney weight to body weight) were also measured for comparison. At the end of chemotherapy (day 33), it was found that both the CDDP alone (Gp II) and the CDDP+MBs+US (Gp III) treatments resulted in significantly greater kidney weight ratios when compared to the control (Gp I) treatment. By contrast, this ratio did not differ significantly for the CDDP-loaded MBs (Gp IV, p=0.86) and CDDP-loaded MBs+US (Gp V, p=0.87) treatments when compared to the control, suggesting that treatment with CDDP-loaded MBs prevented cisplatin-induced increases in kidney weight ratios.

In view of the Examples described hereinbefore, these Examples highlight that conjugation of CDDP with MBs decreases CDDP cytotoxicity for tumor cells both in vitro and in vivo, but a similar antitumor effect is achieved when combined with US exposure. Likewise, the use of CDDP+MBs+US to increase cell permeability and to enhance CDDP uptake and apoptosis, resulting in a better tumor reduction as compared with the conventional CDDP treatments.

Unlike prior art where albumin mesospheres were directly used to load with CDDP and an organic solvent (DMSO) was used to enhance loading efficiency, the CDDP-MBs disclosed herein are prepared in normal saline solution and are comprised of perfluorocarbon gas that is encapsulated in a serum albumin shell. In general, gas bubbles without a shell encapsulation are quite unstable in the bloodstream and may quickly dissolve; shell-free MBs could not even pass through the lung vasculature. Modern MBs each usually includes or consists of two parts: a core with an inert and low soluble gas such as perfluorocarbon or perfluoropropane, and a stabilizing shell, such as phospholipids, proteins, and polymers. In the prior art, engineering of the MB surface architecture and chemistry to reduce complement activation and phagocytosis or directly modifying the lipid shell helps to delay dissolution and ensure a longer half-life of the MBs in circulation. For some preparations, the prolonged circulation time may improve from many minutes up to 1 h. In the present disclosure, although the loading efficiency of CDDP onto the CDDP-MBs was limited to about 10%, the ultrasound-mediated destruction of these CDDP-MBs with an inert gas core preserved the effective cytotoxicity of CDDP without concerns about additional modifications or incorporation of other agents. To the best of our knowledge, this is the first study to prepare gas-filled and CDDP-carrying MBs for the application in cancer chemotherapy.

Figure 12:
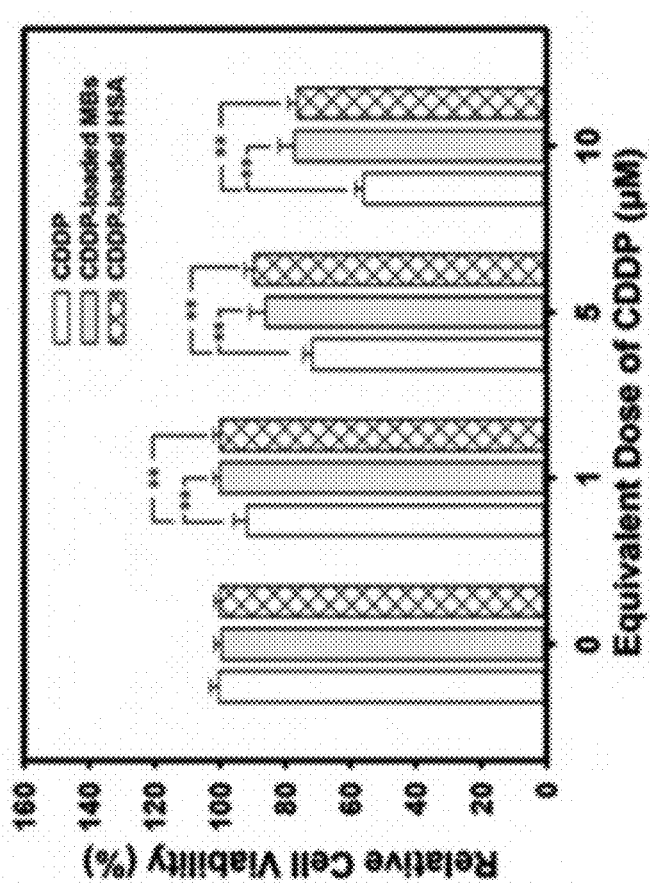
FIG. 12 is a chart showing the comparison of cell viability between different forms of cisplatin at different cisplatin concentrations according to various examples.

Although the platinum (Pt) of CDDP relies on its chloride ligands to enter cells when circulated in the bloodstream that contains high concentrations of chloride, only 10% of the introduced CDDP can enter into the cells, as 90% becomes bound to the plasma proteins. Our results demonstrate that CDDP, when bound within albumin MBs, is rendered inactive and less toxic. The binding of CDDP to the MBs diminished its cytotoxicity, and CDDP loaded onto HSA also significantly decreased its cytotoxicity in FaDu cells. The experiment results are shown in FIG. 12. These results are consistent with previous studies that investigated the antitumor activity and toxicity of protein-bound CDDP complexes. A phase I study of patients with head and neck cancers has shown that a cisplatin-albumin complex, either at a starting dose of 100 mg/m2 or a gradually escalated dose to 650 mg/m2, caused no significant nephrotoxicity or ototoxicity in publication. The CDDP-albumin complex is not as effective as conventional therapy, so, not surprisingly, the patients treated with the complex have a shorter median survival time when compared with patients receiving conventional CDDP therapy (109 days vs. 151 days). The present disclosure is attempted to overcome this drawback by diminishing the systemic side effects of chemotherapy using CDDP-loaded MBs, while enhancing their antitumor activity using ultrasound. The results disclosed herein showed that nephrotoxicity is minimized by administration of CDDP-loaded MBs when compared to conventional CDDP. CDDP-loaded MBs treatment or CDDP+MBs treatment followed by ultrasound (US) exposure leads to antitumor effects similar to or even better than that was treated with conventional CDDP therapy. The combination of CDDP, MBs, and US shows the greatest tumor reduction through USMB-mediated cavitation effects on the tumor cells. Thus, ultrasound treatment gives CDDP enough momentum to travel within the tumor without affecting the cytotoxicity of free CDDP.

Several known risk factors, such as hypomagnesemia, cardiac disease, and hypoalbuminemia have been associated with cisplatin-induced nephrotoxicity. Cancer patients are known to have relatively decreased plasma albumin levels when compared to healthy subjects. Patients with lower albumin levels are prone to have a higher unbound fraction of plasma CDDP and a reduced CDDP half-life. Hypoalbuminemia may also affect the peritubular oncotic pressure and in turn affect Pt excretion, thereby putting these patients at greater risk of nephrotoxicity. A recent in vitro study of plasma protein and distribution of Pt by Morris et al. reported an increase in toxic CDDP-derived hydrolysis products and a decrease in protein bound Pt in the plasma of pediatric cancer patients with low serum albumin, when compared to plasma from healthy controls. Interestingly, an increase in the concentration of plasma serum albumin resulted in a decrease in the CDDP-derived hydrolysis products, suggesting that reinforcement of the plasma albumin concentration in cancer patients prior to CDDP treatment could be a simple strategy for alleviation of CDDP-induced toxic side effects.

Figure 13B:
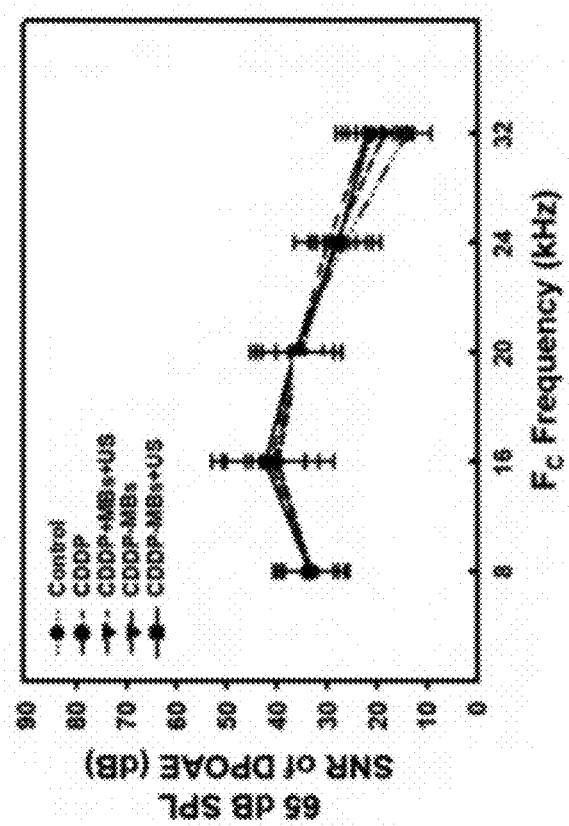
FIG. 13B is a chart showing the signal-to-noise ratio (SNR) of the distortion product (DP) according to some examples.
Figure 13A:
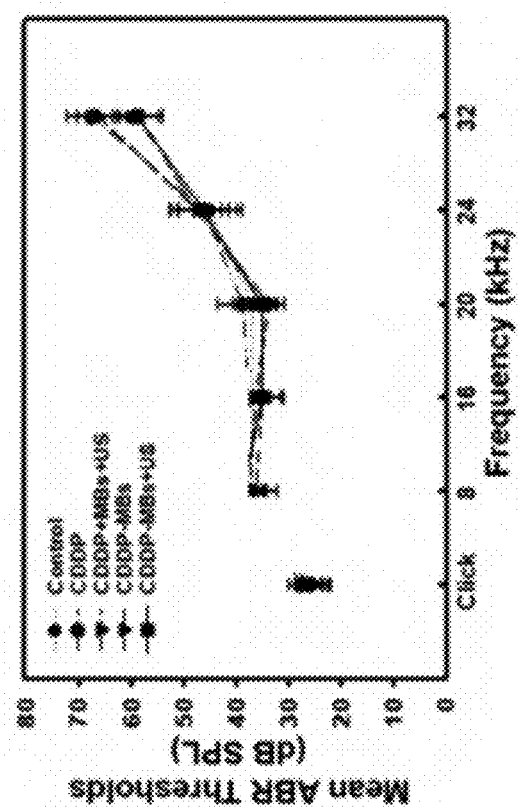
FIG. 13A is a chart showing the ABR thresholds according to some examples.

Patients treated with Pt analogues are also thought to be at high risk for developing hearing loss. The embodiments of the present disclosure shows that the lowest Pt content of all analyzed organs is in the inner ear, and hearing assessment, as tested by the combined use of ABR and DPOAE, revealed no significant differences in the hearing thresholds and signal-to-noise ratio (SNR) of the distortion product (DP) measurements at frequencies from 4 kHz to 32 kHz among the treatment and control groups. The experimental results are shown in FIGS. 13A and 13B. Astolfi et al. demonstrated that intraperitoneal injection of CDDP at a single high dose of 14 mg/kg or at 4.6 mg/kg/day for three consecutive days caused a hearing threshold shift in rats. In the present disclosure, a low dose of CDDP at 2 mg/kg twice a week is used, which might have effects that are too subtle for evaluating CDDP-induced hearing loss in mice. Nevertheless, this implies that the side effect of hearing loss may be avoided according to the embodiments of the present disclosure.

The use of CDDP-bound MBs plus ultrasound treatment appears to have several advantages over existing chemotherapy methods, as the CDDP-MBs are less toxic than CDDP alone, the treatments are simple to perform, and most importantly, the CDDP-MBs are designed for systemic application. Local injection of CDDP and MBs, followed by US exposure of localized lymph nodes and tumors, has also demonstrated several benefits over conventional CDDP, but the pitfalls of this approach may include possible major blood vessel injury, restricted delivery to the injection site, and limited CDDP penetration due to the intratumoral interstitial pressure. Treatment of advanced stages of SCCHN also requires a more sophisticated systemic chemotherapy approach than a local approach in terms of extended locoregional control and ameliorating the rate of distant metastasis.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A cisplatin-loaded microbubble prepared by the following steps: (a) mixing an albumin, a cisplatin, and a medium to form an initial mixture, wherein the initial mixture has a cisplatin concentration ranged from 1-12 mg/mL, and a concentration ratio of the cisplatin and the albumin ranges from 1:22 to 1:25; and (b) introducing an inert gas and applying an ultrasonic oscillating treatment to the initial mixture to form the cisplatin-loaded microbubble, the cisplatin-loaded microbubble comprising:
    a shell portion comprising a plurality of albumin molecules and a plurality of first cisplatin molecules covalently bonded to the albumin molecules; and
    a core portion being surrounded by the shell portion, wherein the core portion comprises a mixture of inert gas and a plurality of second cisplatin molecules.

2. The cisplatin-loaded microbubble of claim 1, wherein an amount of the first cisplatin molecules is greater than an amount of the second cisplatin molecules, and the second cisplatin molecules are free of covalently bonding with the albumin molecules of the shell portion.

3. The cisplatin-loaded microbubble of claim 1, wherein the inert gas is selected from the group consisting of perfluoropropane ($C_3F_8$) gas, sulfur hexafluoride ($SF_6$) gas, and a combination thereof.

4. The cisplatin-loaded microbubble of claim 1, wherein the cisplatin-loaded microbubble has a diameter ranged from about 0.6 μm to about 10 μm.

5. The cisplatin-loaded microbubble of claim 1, wherein the core portion consists essentially of the inert gas and the second cisplatin molecules.

6. A pharmaceutical composition for treatment of cancer prepared by the following steps: (a) mixing an albumin, a cisplatin, and a medium to form an initial mixture, wherein the initial mixture has a cisplatin concentration ranged from 1-12 mg/mL, and a concentration ratio of the cisplatin and the albumin ranges from 1:22 to 1:25; and (b) introducing an inert gas and applying an ultrasonic oscillating treatment to the initial mixture to form a plurality of cisplatin-loaded microbubbles, the pharmaceutical composition comprising:
    the medium; and
    the cisplatin-loaded microbubbles dispersed in the medium, each cisplatin-loaded microbubble comprising:
        a shell portion comprising a plurality of albumin molecules and a plurality of first cisplatin molecules covalently bonding to the albumin molecules; and
        a core portion surrounded by the shell portion, wherein the core portion comprises a mixture of inert gas and a plurality of second cisplatin molecules.

7. The pharmaceutical composition of claim 6, wherein the medium comprises physiological saline.

8. The pharmaceutical composition of claim 6, wherein the core portion consists essentially of the inert gas and the second cisplatin molecules.

9. The pharmaceutical composition of claim 6, wherein the second cisplatin molecules are free of covalently bonding with the albumin molecules of the shell portion.

10. The pharmaceutical composition of claim 6, wherein a ratio of the first cisplatin molecules to the albumin molecules ranges from about 10 to about 25.

11. The pharmaceutical composition of claim 6, wherein the pharmaceutical composition has a cisplatin concentration ranged from about 250 to about 450 μg/mL.

12. The pharmaceutical composition of claim 6, wherein an amount of the first cisplatin molecules is greater than an amount of the second cisplatin molecules.

13. The pharmaceutical composition of claim 6, wherein the cisplatin-loaded microbubbles are present at a concentration ranged from $0.5$-$3\times10^8$ particles/mL in the composition.

14. The pharmaceutical composition of claim 6, wherein an average diameter of the cisplatin-loaded microbubbles ranges from about 0.6 μm to about 10 μm.

15. A method for preparing a pharmaceutical composition, the method comprising:
    mixing albumin and cisplatin with saline to form a mixture, wherein the cisplatin is covalently bonded to the albumin, the mixture has a cisplatin concentration ranged from 1-12 mg/mL, and a concentration ratio of the cisplatin and the albumin ranges from 1:22 to 1:25; and
    introducing inert gas and applying an ultrasonic oscillating treatment to the mixture to form a plurality of cisplatin-loaded microbubbles therein, each of the cisplatin-loaded microbubbles comprising a shell portion and a core portion surrounded by the shell portion, wherein the shell portion comprises the albumin and a first portion of the cisplatin covalently bonded to the albumin molecules, and the core portion comprises a mixture of inert gas and a second portion of the cisplatin.

16. The method of claim 15, wherein the mixture has an albumin concentration ranged from 125-155 mg/mL.

17. The method of claim 15, further comprising incubating the mixture for a time period of 2 hours to 48 hours before introducing the inert gas and applying the ultrasonic oscillating treatment to the mixture.

18. The method of claim 15, wherein the inert gas is selected from the group consisting of perfluoropropane ($C_3F_8$) gas, sulfur hexafluoride ($SF_6$) gas, and a combination of thereof.

19. The method of claim 15, wherein the pharmaceutical composition consists essentially of the albumin, the cisplatin, the saline and the inert gas.

20. The method of claim 15, wherein the cisplatin-loaded microbubbles have an averaged diameter ranged from about 0.6 μm to about 10 μm.

21. The method of claim 15, wherein a concentration of the cisplatin-loaded microbubbles is ranged from about $0.1\times10^8$ to about $2.5\times10^8$ particles/mL.

22. A method for treating cancer, the method comprising:
    administering the pharmaceutical composition as claimed in claim 6 to a subject in need; and
    applying ultrasound energy to a tumor of the subject to break the cisplatin-loaded microbubbles.

23. The method of claim 22, wherein the cancer is squamous cell cancer.

24. The method of claim 22, wherein the ultrasound energy has a power of 1 W to 3 W.

25. The method of claim 22, further comprising determining a cisplatin concentration in a non-target tissue of the subject and a cisplatin concentration in a tissue of the tumor.

26. The method of claim 25, wherein the cisplatin concentration of the non-target tissue is less than the cisplatin concentration of the tissue of the tumor.

27. The method of claim 26, wherein the non-target tissue is a liver tissue.

28. The method of claim 26, wherein the non-target tissue is a kidney tissue.

29. The method of claim 22, wherein the composition has an albumin concentration of about 580-7600 mg/m$^2$.

30. The method of claim 22, wherein the composition has a cisplatin concentration of about 50-650 mg/m$^2$.

* * * * *